(12) United States Patent
Wish

(10) Patent No.: US 7,802,575 B2
(45) Date of Patent: Sep. 28, 2010

(54) CONDOM PACKAGING

(76) Inventor: Jerrold Alan Wish, 245 N. Coconut La., Miami Beach, FL (US) 33139

( * ) Notice: Subject to any disclaimer, the term of this patent is extended or adjusted under 35 U.S.C. 154(b) by 0 days.

(21) Appl. No.: 12/185,590

(22) Filed: Aug. 4, 2008

(65) Prior Publication Data

US 2009/0134045 A1 May 28, 2009

Related U.S. Application Data

(63) Continuation of application No. 11/945,232, filed on Nov. 26, 2007.

(51) Int. Cl.
*A61F 6/02* (2006.01)
(52) U.S. Cl. .................. 128/842; 128/844; 602/902
(58) Field of Classification Search .............. 128/842, 128/844; 602/902; 604/347–353
See application file for complete search history.

(56) References Cited

U.S. PATENT DOCUMENTS

| | | | | |
|---|---|---|---|---|
| 2,321,254 | A * | 6/1943 | Schmid | 206/69 |
| 5,170,887 | A | 12/1992 | Potts et al. | |
| 5,437,286 | A * | 8/1995 | Stratton | 128/844 |
| 5,477,865 | A * | 12/1995 | Broad, Jr. | 128/844 |
| 5,651,374 | A | 7/1997 | Wester | |
| 5,666,972 | A * | 9/1997 | Gifford | 128/842 |
| 5,803,245 | A | 9/1998 | Wood | |
| 6,929,118 | B1 | 8/2005 | Izz | |
| 2002/0069881 | A1 | 6/2002 | Kassman | |

OTHER PUBLICATIONS

U.K. Search Report for related U.K. patent application No. 01633813753. Japan Medical One Touch Condom, http://www.youtube.com/watch?v=6wavbLHP4JA, http://www.japanmedical.com.hk/pub/productpage/otc.htm.
Japan Medical One Touch Condom, http://www.youtube.com/watch?v=6wavbLHP4JA, http://www.japanmedical.com.hk/pub/productpage/otc.htm.

* cited by examiner

*Primary Examiner*—Michael A. Brown
(74) *Attorney, Agent, or Firm*—O'Brien Jones, PLLC

(57) ABSTRACT

A condom packaging and method of donning a condom are disclosed. The condom packaging has a top layer and a bottom layer, which are attached along two opposing sides. The opposing sides of the condom packaging may be squeezed to cause the packaging material and the condom to take a cylindrical shape to aid in donning the condom. In the method of donning a condom, a condom enclosed in a condom package is provided. The condom package has a packaging material surrounding the condom and is substantially flat with a top layer, a bottom layer, and two opposed sides. The opposed sides of the packaging material can be squeezed to cause the packaging material and the condom to take a cylindrical shape. The condom can then be donned and the condom package may be removed.

3 Claims, 6 Drawing Sheets

CONDOM PACKAGING

This is a continuation of U.S. patent application Ser. No. 11/945,232, filed Nov. 26, 2007, which is incorporated herein by reference in its entirety.

FIELD

The present invention relates generally to condom packaging, and more particularly to a device for packaging and donning condoms.

INTRODUCTION

The recent significant increase in the incidence and spread of sexually transmitted diseases (STD's) has resulted in increased use of condoms as a prophylactic measure to reduce the risk of infection and transmission of STD's.

Condoms generally comprise elongated thin, flexible, tubular sheaths made of a resilient, rubber-like material, such as rubber or various thermoplastic elastomers. Condoms are often difficult for the user to put on due to the small size of the device opening, and the resistance to stretching of the open end of the device, which typically comprises an annular ring designed for a tight fit.

During manufacture, condoms made of rubber or other stretchable materials are typically rolled, which makes them easier to package, store, and apply. Even when condoms are so packaged, donning rolled condoms is difficult because the user must pull the rubbery opening area apart and widen the opening with his fingers to don the condom. Further, many condoms are sold with a lubricant coating or spermicide thereon, which often makes it difficult to grasp the condom prior to and during the donning of the condom.

Due to its prophylactic nature, it is important to avoid puncturing the condom during its removal from the packaging and application by the user. Punctures or tears provide gaps in the prophylactic defense of the condom and can allow the transmittal of fluids that increase the risk of transmitting sexually transmitted diseases or increase the chances of an unplanned pregnancy. The more a condom is handled by the user, the greater the likelihood that the condom will be damaged. Thus, it is desirable to decrease the amount of handling by the user during the application of the condom.

One condom package designed to allow application of the condom without requiring the user to touch the condom is disclosed in Suzuki (U.S. Pat. No. 6,718,983), wherein fitting tapes are rolled with the condom when packaged. When the user opens the packaging, the fitting tapes hold the condom in position for application while the user holds the external packaging structure.

The structures of the open end of condoms have been varied, for example, by widening the opening, to attempt to make it easier to don condoms, while still providing devices that do not inadvertently slip out of place.

Packing procedures and devices utilizing resilient rings to assist in donning surgical gloves are disclosed in Poncy et al. (U.S. Pat. No. 4,275,812), wherein the cuff of each surgical glove is contained in a cylindrical ring, which holds the glove open to aid in donning the glove. The cylindrical ring also contains the mouth of a bag that encloses the outer surface of the glove to maintain sterility prior to use. The glove cuff is released from the ring, and the ring and bag are removed after the surgeon has put on the gloves.

SUMMARY

The present invention may address one or more of the above-mentioned issues. Other features and/or advantages may become apparent from the description which follows.

Certain embodiments of the present teachings provide a condom packaging comprising a top layer and a bottom layer, wherein the top layer and the bottom layer are attached along two opposing sides. The opposing sides of the condom packaging may be squeezed to cause the packaging material and the condom to take a cylindrical shape to aid in donning the condom.

Certain embodiments of the present teachings alternatively or additionally provide a method of donning a condom, comprising providing a condom enclosed in a condom package, wherein the condom package comprises a packaging material that surrounds the condom and is substantially flat with a top layer, a bottom layer, and two opposed sides. The opposed sides of the packaging material can be squeezed to cause the packaging material and the condom to take a cylindrical shape. The condom can then be donned and the condom package may be removed.

In the following description, certain aspects and embodiments will become evident. It should be understood that the invention, in its broadest sense, could be practiced without having one or more features of these aspects and embodiments. It should be understood that these aspects and embodiments are merely exemplary and explanatory and are not restrictive of the invention.

BRIEF DESCRIPTION OF THE DRAWINGS

Features and advantages of the claimed subject matter will be apparent from the following detailed description of embodiments consistent therewith, which description should be considered with reference to the accompanying, wherein:

Although the following detailed description makes reference to illustrative embodiments, many alternatives, modifications, and variations thereof will be apparent to those skilled in the art. Accordingly, it is intended that the claimed subject matter be viewed broadly.

DETAILED DESCRIPTION OF VARIOUS EMBODIMENTS

Reference will now be made to various embodiments, examples of which are illustrated in the accompanying drawings. However, these various exemplary embodiments are not intended to limit the disclosure. To the contrary, the disclosure is intended to cover alternatives, modifications, and equivalents.

The present teachings contemplate methods and embodiments for packaging varied types and styles of condoms, including those that are not rolled up in the usual manner and those that include lubricants and other complimentary liquids, wherein the packaging can serve as a mechanical applicator to simplify donning the condom.

The condom positioned within a packaging in accordance with the present teachings may be of any known structure and formed via any method known in the art, including molding, extrusion, heat sealing, or dipping.

The condom package may be made of paper, foils, or plastics, as well as any combination thereof, such as foil-lined paper, plastic-lined paper or a wax-lined paper. The package may take a variety of forms such as rectangular, oval, etc. The package may be provided with a separation structure, such as an edge tear area, a zipper-locked edge area, or an openable, adhesively sealed edge area.

EXAMPLE I

Figure 1:
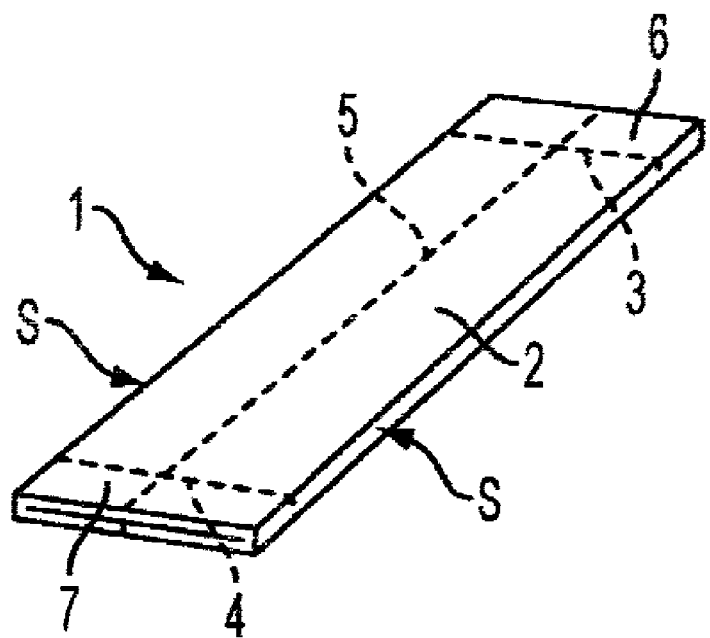
FIG. 1 is a perspective view of a condom package according to an embodiment of the present teachings in a sealed position.

In accordance with certain embodiments of the present teachings, flanged condom 8 of a selected thermoplastic elastomer material, such as a polyester-based polyurethane or polyurethane elastomer (e.g. ELASTOLLAN®) can be used (FIG. 1). Two roughly rectangular pieces of foil-lined paper 2 can be prepared with a separate piece of adhesive tape or compatible adhesive material attached at one end to an interior foiled side of each piece of paper. A remaining end of each piece of adhesive tape can be attached to one of the flanges of the condom 8 forming an attachment point 9. The tubular end T of the condom is rolled up or folded, and placed beneath the condom open end.

The two pieces of packaging material 2 can be placed together with the condom therebetween and edge portions 6, 7 of the two pieces of packaging material 2 can be attached together (see FIG. 3), such as with an adhesive. In other embodiments, the packaging material can be one piece of packaging material. The two pieces of packaging material 2 can be adhered before a condom is placed inside. The adhesive along one of the edge portions 6, 7 (e.g., at the attachment point 9 of the condom) is spaced in from the edge, to provide an unglued package edge portion 7 for gripping and opening the package for use.

Figure 2:
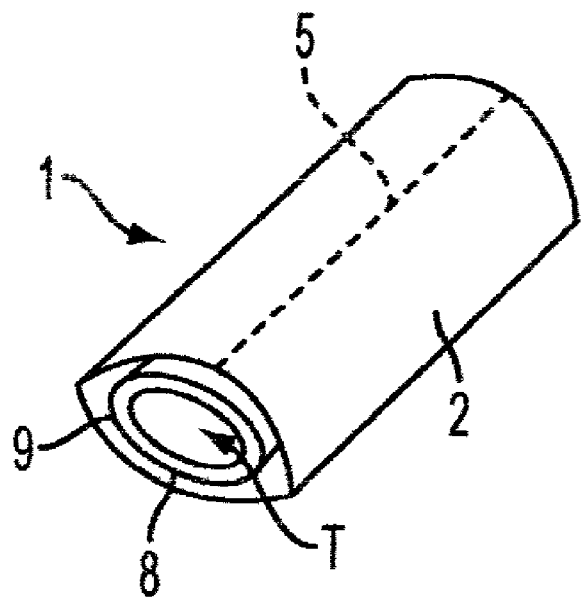
FIG. 2 is a perspective view of a condom package according to the embodiment of FIG. 1 in an application position.

The edge portions 6, 7 of packaging material 2 can be separated from the central portion of packaging material 2 by perforated areas 3, 4 to allow the edge portions 6, 7 to be removed. To don the condom, edge portions 6, 7 can be torn off by the user. The user can then squeeze the sides S of the flattened packaging material 2 to form a substantially cylindrical condom package 1 (see FIG. 2). The tubular end T of condom 8 follows the packaging into an open application position due, for example, to the adhesion of the flanges of condom 8 to attachment point 9. The user can then don the condom 8 by sliding the condom applicator 1 over the penis. Once the condom 8 has been donned, the user can then remove the packaging material 2 by tearing the packaging material along perforation 5. Perforation 5 is positioned substantially parallel to opposing sides S to assist the user in the removal of the packaging after the condom has been donned.

While Example 1 discloses a single embodiment of the invention, other embodiments other embodiments of the disclosure will be apparent to those skilled in the art from consideration of the specification and practice of the teachings disclosed herein.

Other exemplary embodiments of the present invention are disclosed in FIGS. 5-12.

Figure 5:
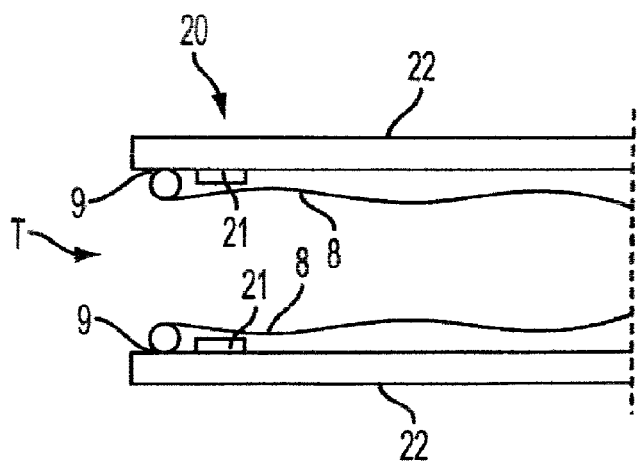
FIG. 5 is a cutaway side view of a condom package according to another embodiment of the present teachings in an application position.
Figure 6:
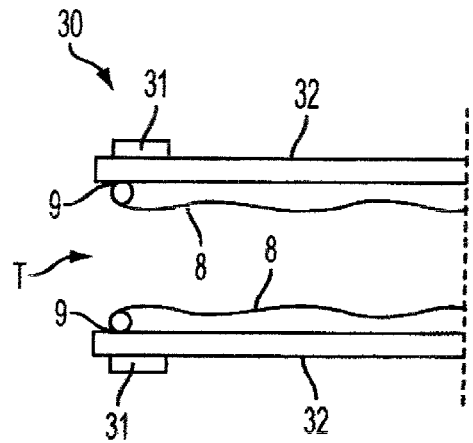
FIG. 6 is a cutaway side view of a condom package according to another embodiment of the present teachings in an application position.

In accordance with certain embodiments of the present teachings, a condom package 20, 30 may comprise expansion member 21, 31 as shown in FIG. 5 and FIG. 6. Expansion member 21, 31 may comprise, for example, metal or plastic. Expansion member 21, 31 provides rigidity to the packaging material 22, 32 at a tubular end T of the condom 8 and may aid in the formation of a circular opening for application. Expansion member 21, 31 may be provided on either the interior or exterior of packaging material 22, 32. In certain embodiments of the present teachings, expansion member 21, 31 may comprise a metal wire. After donning the condom, expansion member 21, 31 can be separated along with the removal structure (not shown) to aid in removal of the condom package 1.

Figure 7:
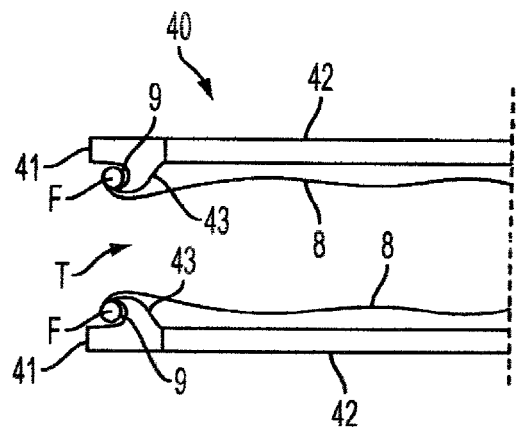
FIG. 7 is a cutaway side view of a condom package according to another embodiment of the present teachings in an application position.

In certain embodiments of the present teachings, attachment point 9 may be formed without the use of adhesives. FIG. 7 shows a condom applicator 40 comprising a hooked fastener 41. The hooked fastener 41 comprises fastening portion 43 which grips the flanges F of condom 8. The hooked fastener 41 may comprise a material such as plastic, which can be adhered or mechanically attached to packaging material 42 in a known manner. After donning the condom, the hooked fastener 41 may be disengaged from condom 8 by opening the packaging material 2 along the removal structure (not shown) and moving the condom packaging in a direction opposite the opening of the hooked fastener.

Figure 8:
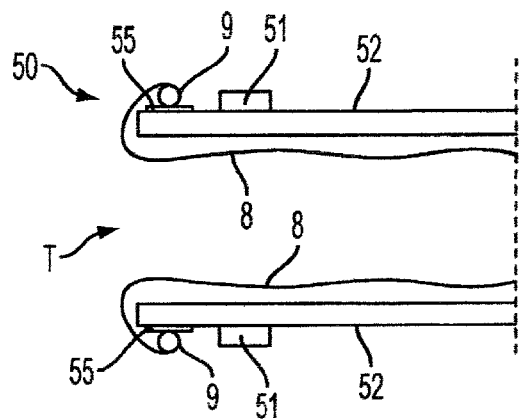
FIG. 8 is a cutaway side view of a condom package according to another embodiment of the present teachings in an application position.
Figure 9:
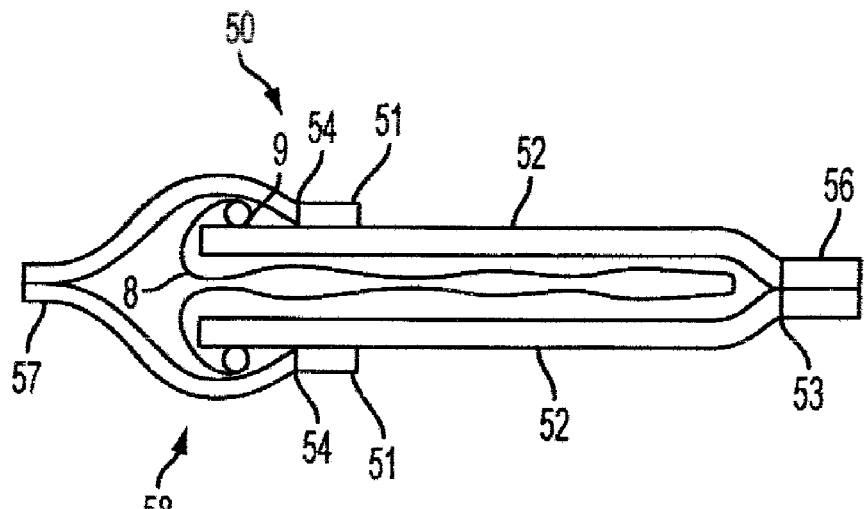
FIG. 9 is a cutaway side view of the condom package according to the embodiment of FIG. 8 in a sealed position.

In certain embodiments of the present teachings, attachment point 9 of condom applicator 50 can be on the exterior of packaging material 52 (see FIG. 8 and FIG. 9). For example, adhesive tape 55 may be applied to an exterior of packaging material 52 and flanges of condom 8 may be affixed to the adhesive tape at attachment point 9. In such embodiments, a removable tab 58 can be attached to the exterior of packaging material 52. Edges 51 of removable tab 58 can be adhered to the exterior of packaging material 52 using know adhesive methods. Perforations 54 may be employed to aid in the removal of removable tab 58 by allowing the user to grasp an edge portion 57 and tear removable tab 58 from condom applicator 50. Edge portion 56 may be removed at perforation 53. After the condom is donned, packaging material 2 and the remaining edge 51 may be removed by tearing the packaging material along a removal structure (not shown).

Figure 10:
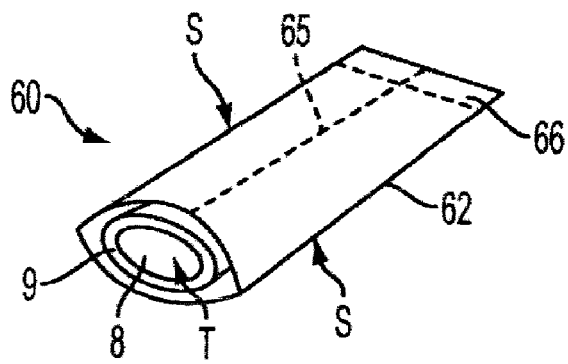
FIG. 10 is a perspective view of a condom package according to yet another embodiment of the present teachings in an application position.

In certain embodiments of the present teachings, a condom package 60 comprises a sealed end 66 (FIG. 10). In this embodiment, condom package 60 is opened only at the tubular end T of condom 8. Once the edge portion adjacent the flanges of condom 8 is removed, the user squeezes the sides S of packaging material 62 to place the condom 8 in a cylindrical shape for donning. After donning the condom, packaging material 2 may be removed by tearing the packaging material along perforation 65.

Figure 11:
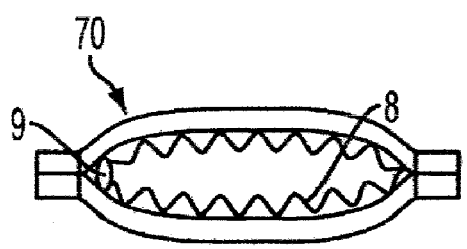
FIG. 11 is a cutaway side view of a condom package according to yet another embodiment of the present teachings in a sealed position.
Figure 12:
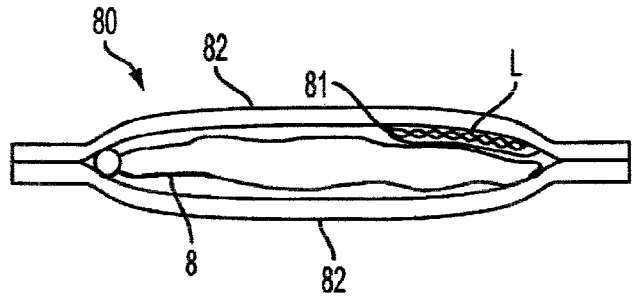
FIG. 12 is a cutaway side view of a condom package according to another embodiment of the present teachings in a sealed position.

Condom 8 may be gathered or it can extend in a generally taut manner with in the condom package. For example, FIG. 1 shows a condom package 1 comprising a taut condom 8, whereas FIG. 11 shows a condom package 70 comprising a gathered condom 8. By gathering the condom, the length of the condom packaging can be decreased to a desired degree. In other embodiments, the entire length of the condom or a portion thereof may be removably adhered to the interior of the packaging material to hold the condom in a substantially cylindrical shape when the sides of the packaging are squeezed.

In certain embodiments of the present teachings, a lubricant or other complimentary liquid may be contained within the condom package. Complimentary liquids may include, for example, spermicides, flavorings, aromatic liquids, warming liquids, etc. For example, in FIG. 3, a lubricant or complimentary liquid may be contained between condom 8 and the interior surface 10 of packaging material 2. The lubricant or complimentary liquid may be contained within a fluid compartment within an interior of the packaging material. For example, in FIG. 12, condom package 80 comprises a lubricant or complimentary liquid L within fluid compartment 81 within an interior of packaging material 82.

Figure 3:
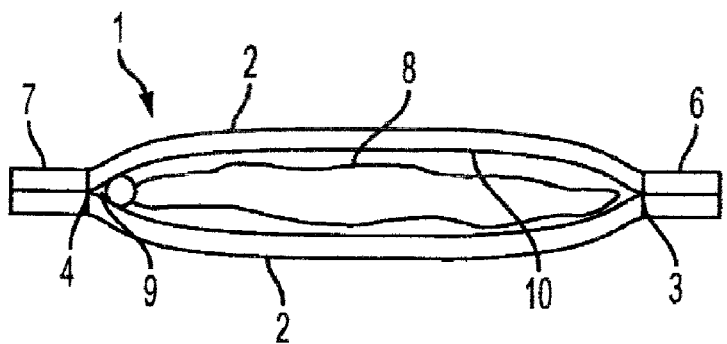
FIG. 3 is a cutaway side view of a condom package according to the embodiment of FIG. 1 in a sealed position.
Figure 4:
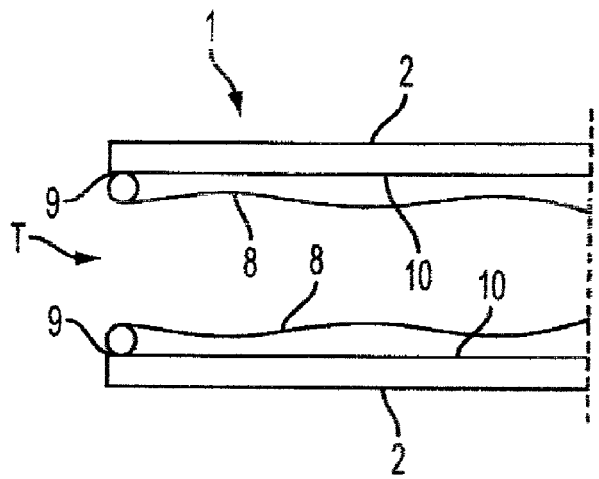
FIG. 4 is a cutaway side view of a condom package according to the embodiment of FIG. 1 in an application position.
Figure 13:
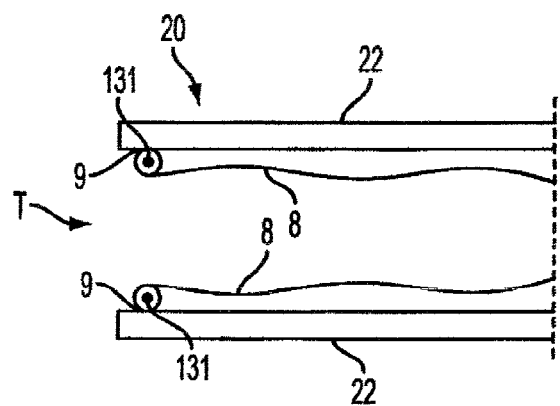
FIG. 13 is a cutaway side view of a condom package according to another embodiment of the present teachings in a sealed position.

FIG. 13 illustrates an exemplary embodiment of the present teachings similar to the embodiment of FIG. 3, but having an expansion member 131 such as, for example, a wire located within a portion of the condom 8 at a tubular end of the condom 8 near the attachment point 9.

Figure 14:
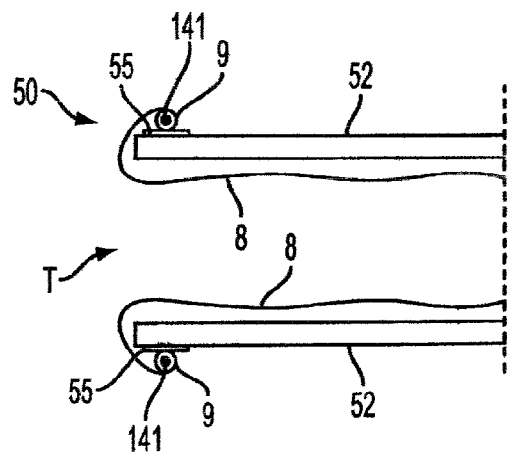
FIG. 14 is a cutaway side view of a condom package according to another embodiment of the present teachings in a sealed position.

FIG. 14 illustrates an exemplary embodiment of the present teachings similar to the embodiment of FIG. 8, but having an expansion member 141 such as, for example, a wire located within a portion of the condom 8 at a tubular end of the condom 8 near the attachment point 9. In the embodiments of FIGS. 13 and 14, the expansion member 131, 141 can remain in or with the condom after the packaging 22 is removed.

Figure 15:
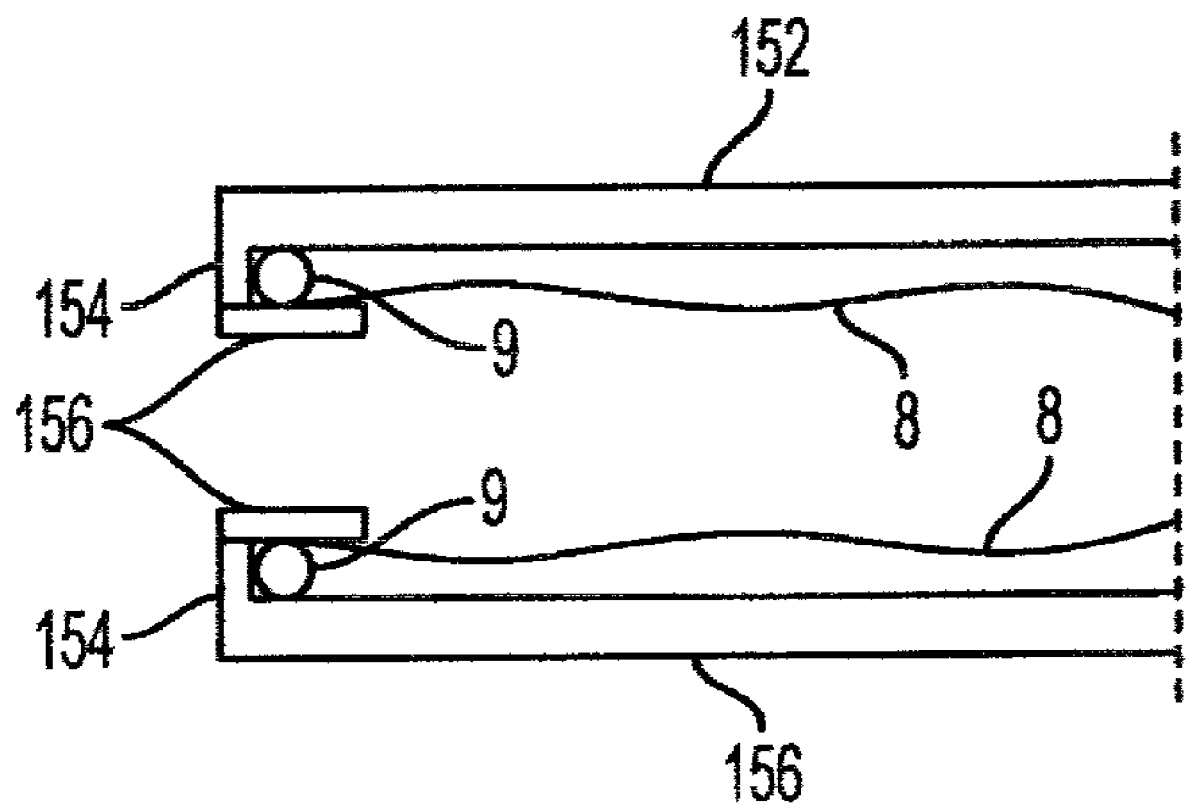
FIG. 15 is a cutaway side view of a condom package according to another embodiment of the present teachings in a sealed position.

FIG. 15 illustrates an exemplary embodiment of the present teachings wherein the packaging material 152 has a portion 154 to which an expansion member 156 is externally attached. The expansion member 156 can be removed with the package or remain attached to the condom after the package is removed. As can be seen in the illustrated exemplary embodiment, portion 154 can extend at an angle from the main portion of the packaging material 152, to extend along the tubular end T of the condom 8. Expansion member 156 can then extend inward into an opening of the tubular end T of the condom 8 for attachment to the condom 8. One skilled in the art will understand that expansion member 156 can have many shapes and sizes, and need not be attached to an inner surface of the tubular end T of the condom 8. Indeed, the expansion member 156 can be located, for example, along an exterior of the condom 8, such as where the portion 154 is presently illustrated or at other suitable locations.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the written description and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "an adhesive" can include two or more different adhesives. As used herein, the term "include" and its grammatical variants are intended to be non-limiting, such that recitation of items in a list is not to the exclusion of other like items that can be substituted or added to the listed items.

It will be apparent to those skilled in the art that various modifications and variation can be made to the sample preparation device and method of the present disclosure without departing from the scope its teachings. Other embodiments of the disclosure will be apparent to those skilled in the art from consideration of the specification and practice of the teachings disclosed herein. It is intended that the specification and examples be considered as exemplary only.

What is claimed is:

1. A method of donning an unrolled condom enclosed in a condom package, wherein the condom package comprises a packaging material that surrounds the unrolled condom and is substantially flat with a top layer, a bottom layer, and two opposed sides, the method comprising:
   squeezing the opposed sides of the packaging material to cause an expansion member of the packaging material and an open end of the condom to move from a flat shape to a cylindrical shape; and
   donning the condom.

2. The method according to claim 1, wherein the condom package further comprises at least one detachable edge portion adjacent the opposed sides of the packaging material, and the method further comprises removing the at least one edge portion prior to donning the condom.

3. The method according to claim 2, wherein the condom package further comprises a removal structure substantially parallel to the opposed sides chosen from a tear area, a zipper-locked area, and an adhesively sealed area, and the method further comprises opening the condom package along the removal structure after donning the condom and before removing the condom package.

* * * * *